United States Patent
Kandelousy

(10) Patent No.: US 9,492,345 B2
(45) Date of Patent: Nov. 15, 2016

(54) SEXUAL NOVELTY FOR MEN'S PLEASURE

(71) Applicant: Sam B Kandelousy, Plano, TX (US)

(72) Inventor: Sam B Kandelousy, Plano, TX (US)

(*) Notice: Subject to any disclaimer, the term of this patent is extended or adjusted under 35 U.S.C. 154(b) by 204 days.

(21) Appl. No.: 13/949,085

(22) Filed: Jul. 23, 2013

(65) Prior Publication Data
US 2015/0141747 A1 May 21, 2015

Related U.S. Application Data

(60) Provisional application No. 61/732,025, filed on Nov. 30, 2012.

(51) Int. Cl.
  *A61H 19/00* (2006.01)
  *A61F 5/41* (2006.01)

(52) U.S. Cl.
  CPC ............... *A61H 19/32* (2013.01); *A61F 5/41* (2013.01); *A61H 2201/0103* (2013.01); *A61H 2201/0153* (2013.01)

(58) Field of Classification Search
  CPC ...... A61H 19/00; A61H 19/32; A61H 19/40; A61H 2201/0207; A61H 2201/0242; A61H 2201/0257
  USPC ...................................... 600/38–41
  See application file for complete search history.

(56) References Cited

U.S. PATENT DOCUMENTS

| | | | |
|---|---|---|---|
| 5,244,454 A | | 9/1993 | Coates |
| 5,458,559 A | * | 10/1995 | Gauntlett ............... 600/38 |
| 5,466,235 A | * | 11/1995 | Shubin, Sr. ............. 600/38 |
| 5,836,865 A | * | 11/1998 | Ritchie et al. ........... 600/38 |
| 6,149,580 A | * | 11/2000 | Dabney ................... 600/38 |
| 7,299,513 B1 | * | 11/2007 | Barrett et al. ............. 5/654 |
| 2006/0264856 A1 | | 11/2006 | Wong |
| 2008/0065187 A1 | | 3/2008 | Squicciarini |
| 2013/0053631 A1 | * | 2/2013 | Kolar .................... 600/38 |

OTHER PUBLICATIONS

Mar. 6, 2014 International Search Report and Written Opinion of Korean Patent Office.

* cited by examiner

*Primary Examiner* — Samuel Gilbert

(57) ABSTRACT

A sexual novelty is configured to pleasure a user by simulating sexual intercourse. The sexual novelty includes a bladder which can be partially filled with air to create a pressure within the bladder. A plurality of cavities are on the bladder and sufficiently sized to accommodate a user's penis. A pump is attached to the bladder which can provide slight increases in the pressure within the bladder in order to create different levels of pressure. The penis can move in and out of a cavity to simulate sexual intercourse while the pump can be used to change the pressure during simulated sexual intercourse.

4 Claims, 4 Drawing Sheets

SEXUAL NOVELTY FOR MEN'S PLEASURE

RELATED APPLICATION

This application claims priority to provisional patent application U.S. Ser. No. 61/732,025 filed on Nov. 30, 2012, the entire contents of which is herein incorporated by reference.

BACKGROUND

The embodiments herein relate generally to devices that can be used for sexual pleasure.

Prior to the disclosed invention sexual novelties were expensive, not disposable, and heavy, this made sexual pleasure for single men and soldiers challenging. The present invention solves these problems.

SUMMARY

A sexual novelty is configured to pleasure a user by simulating sexual intercourse. The sexual novelty includes a bladder which can be partially filled with air to create a pressure within the bladder. A plurality of cavities are on the bladder and sufficiently sized to accommodate a user's penis. A pump is attached to the bladder which can provide slight increases in the pressure within the bladder in order to create different levels of pressure. The penis can move in and out of a cavity to simulate sexual intercourse while the pump can be used to change the pressure during simulated sexual intercourse.

In some embodiments, the plurality of cavities have different sizes to accommodate different cavity preferences. An inlet is mechanically coupled to the bladder and detachably coupled to a stopper. The stopper can be removed permitting partial inflation of the bladder with a water source. An outlet can be mechanically coupled to the bladder and detachably coupled to a second stopper. The second stopper can be removed permitting partial deflation of the bladder.

In some embodiments, laces can be mechanically coupled to the bladder. A second bladder mechanically coupled to second laces such that the bladder can be mechanically coupled to the second bladder by tying the laces.

BRIEF DESCRIPTION OF THE FIGURES

The detailed description of some embodiments of the invention is made below with reference to the accompanying figures, wherein like numerals represent corresponding parts of the figures.

DETAILED DESCRIPTION OF CERTAIN EMBODIMENTS

Figure 1:
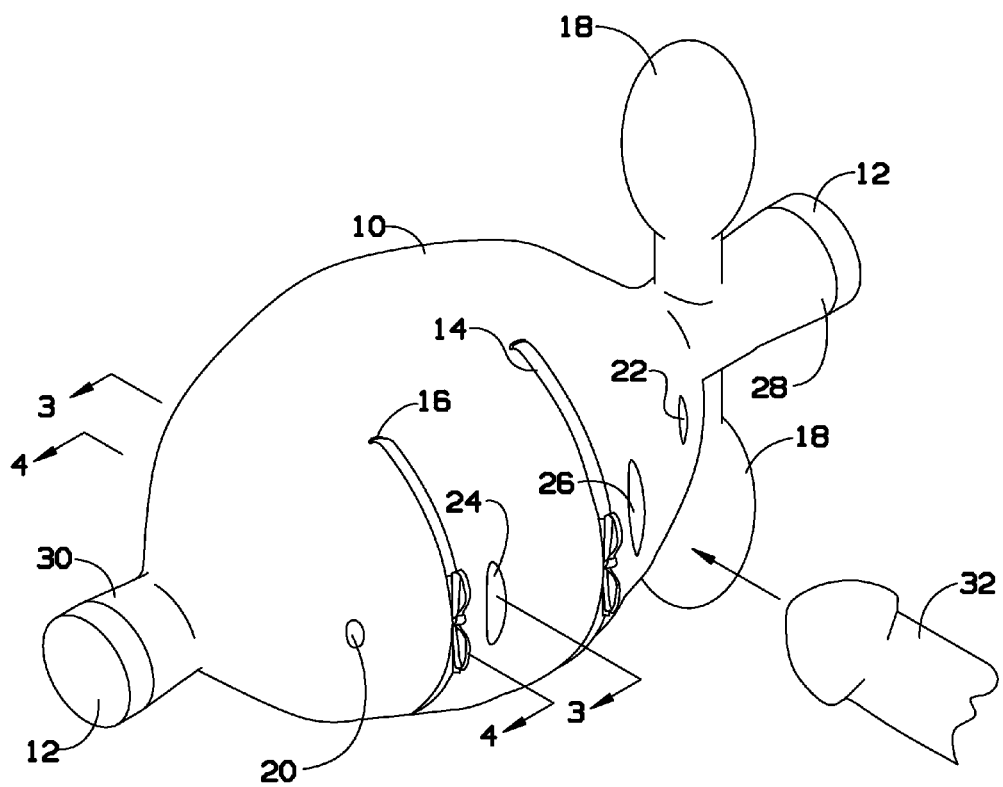
FIG. 1 is a perspective view of the invention inflated.
Figure 3:
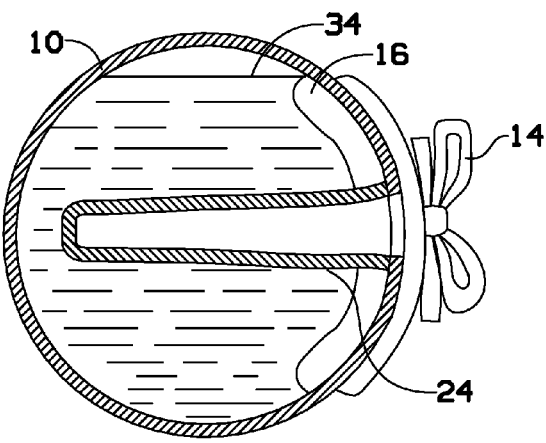
FIG. 3 is a section view of the invention, taken along line 3-3 in FIG. 1.
Figure 4:
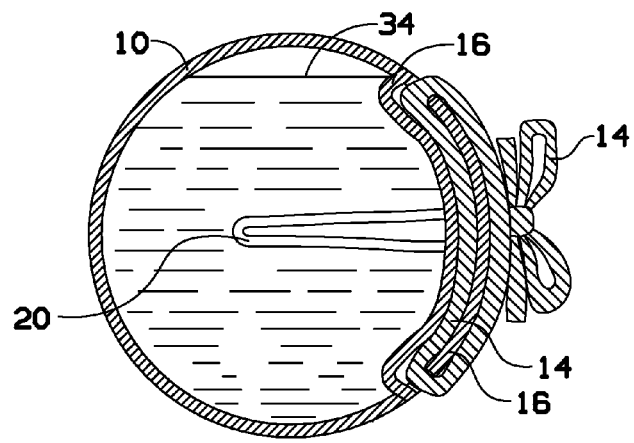
FIG. 4 is a section view of the invention, taken along line 4-4 in FIG. 1.
Figure 5:
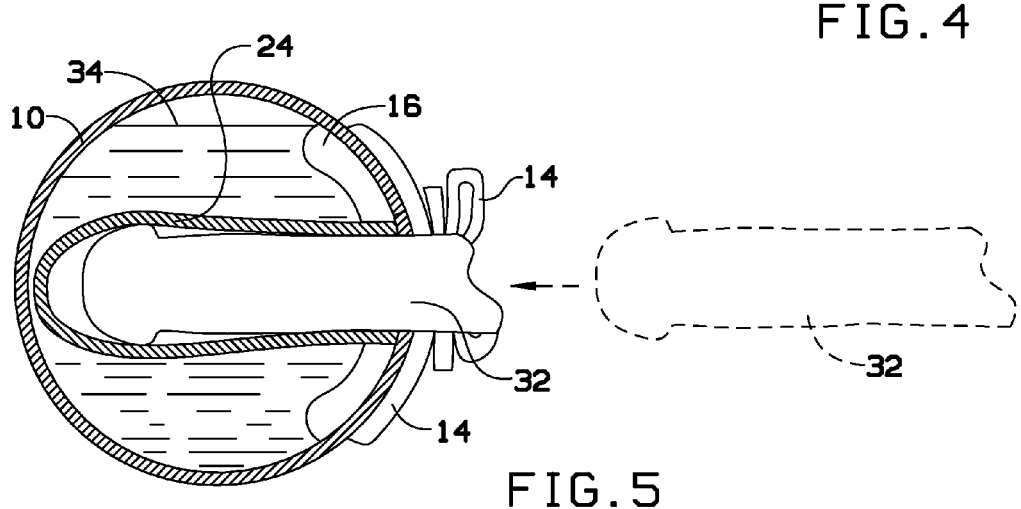
FIG. 5 is a section view of the invention, illustrating the insertion of the user's penis into the large bladder cavity

By way of example, and referring to FIG. 1, one embodiment of the present system comprises bladder 10. Bladder 10 comprises inlet 28 and outlet 30 each enclosed with stopper 12 in some embodiments. Bladder 10 comprises multiple layers as shown in FIG. 3, FIG. 4 and FIG. 5 below. Bladder 10 can utilize laces 14 to increase or decrease pressure inside of bladder 10. Laces 14 are inserted through lace slots 16 ash shown in FIG. 4. Pressure can also be adjusted by compressing pump 18 mechanically coupled to inlet 28 as shown in more detail in FIG. 8.

Bladder 10 comprises a series of cavities of varying size to accommodate a variety of users 32 that can have different cavity preference. For example, the embodiment displayed comprises small cavity 20, medium cavity 22, large cavity 24 and extra-large cavity 26. In some embodiments, the plurality of orifices can have a diameter of ¾ inch, 1 inch, 1½ inch and ½ inch to accommodate different cavity preferences of users 32.

FIG. 3, FIG. 4 and FIG. 5 show section views of bladder 10. Bladder 10 can be partially filled with water 34 and air as noted above. Laces 14 can be inserted through lace slots 16 and tied to increase or decrease pressure as desired. A user inserts penis 32 into large cavity 24, for instance and then pump 18 can provide slight increases in pressure within bladder 10 in order to create different levels of pressure to pleasure user 32. Penis 32 can move in and out of a cavity to simulate sexual intercourse while pump 18 can be used to change the pressure during the simulated sexual intercourse.

Figure 2:
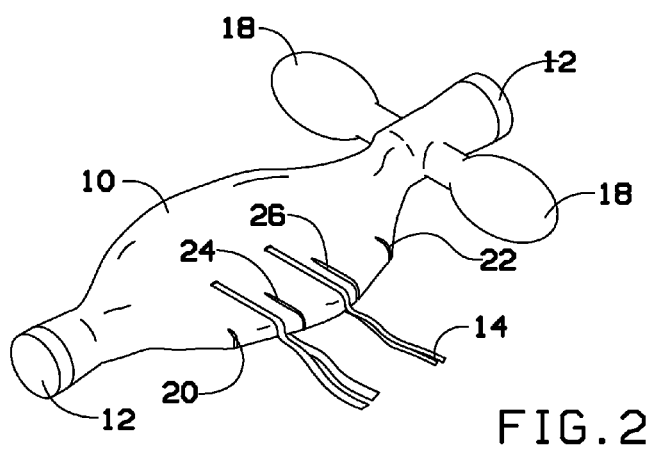
FIG. 2 is a perspective view of the invention deflated.
Figure 6:
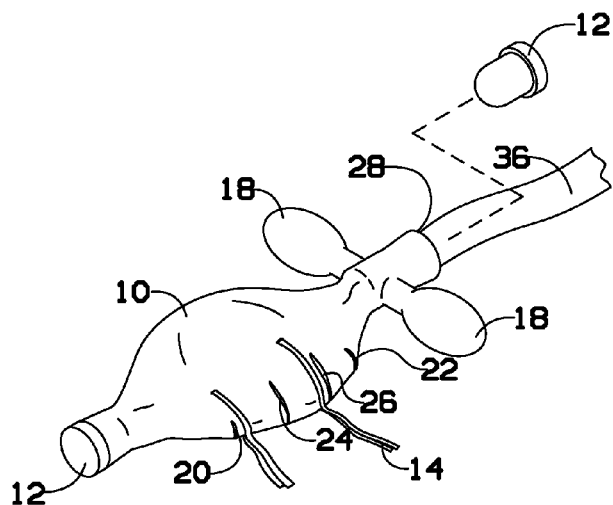
FIG. 6 is a perspective view of the invention, illustrating the bladder being filled with water.
Figure 7:
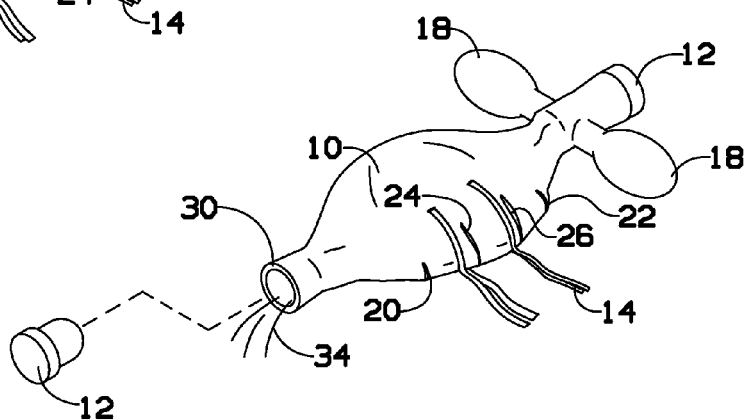
FIG. 7 is a perspective view of the invention, illustrating the draining or deflating of the bladder.

FIG. 2, FIG. 6, FIG. 7 and FIG. 8 show perspective views of how to use the sexual novelty. Bladder 10 typically rests in a deflated form as shown in FIG. 2 with laces 14 untied that can be useful for cleaning small cavity 20, medium cavity 22, large cavity 24 and extra-large cavity 26. Bladder 10 can be inflated with water by removing the stopper 12 at inlet 28 and partially filling bladder 10 with water 34 from fill hose 36 or any other water source as shown in FIG. 6. Likewise, bladder 10 can be deflated with water by removing the stopper 12 at outlet 30 and partially removing water 34 or air from bladder 10 as shown in FIG. 7.

Figure 8:
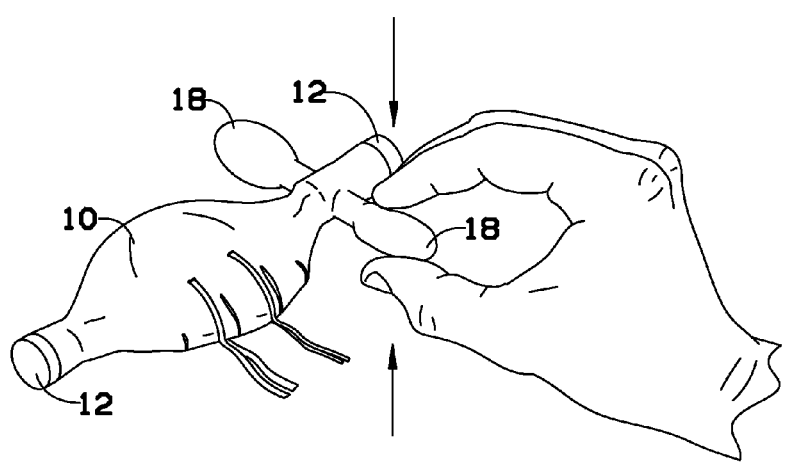
FIG. 8 is a perspective view of the invention, illustrating the alternative use of the bladder pump to fill the bladder with air

FIG. 8 shows one advantage over the prior art has to do with the nature of simulating sexual intercourse. During sexual intercourse penis 32 expands, contracts, grows, shrinks and prefers pressure in a variety of different areas. The prior art does not have a good theory to accommodate this. However, embodiments of the present invention teaches that minor increases in pressure within bladder 10 can be accomplished by pumping a small amount of air into bladder 10 with pump 18. This can simulate the movement of muscles in a body orifice that can better simulate sexual intercourse than the prior art.

Figure 9:
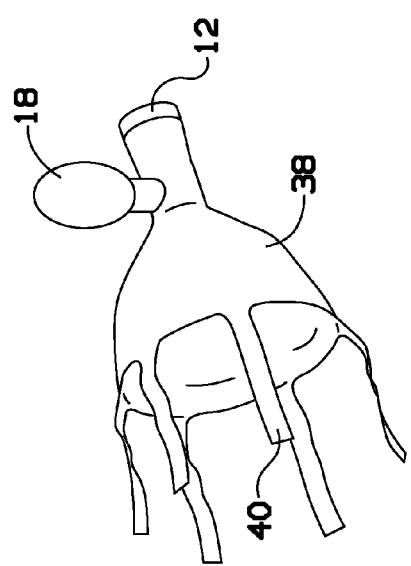
FIG. 9 is a perspective view of an alternate embodiment of the invention, illustrated with the laces untied.
Figure 10:
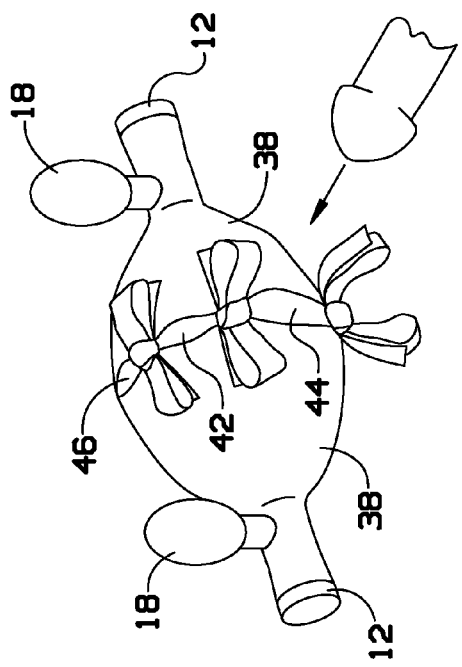
FIG. 10 is a perspective view of an alternate embodiment of the invention with the laces tied.

Water 34, while useful in some embodiments, in not necessary as shown in FIG. 9 and FIG. 10. In this embodiment of the sexual novelty, first bladder 38 is mechanically coupled to first laces 40. First bladder 38 is mechanically coupled to first stopper 12 at an inlet with first pump 18. Likewise, second bladder 38 is mechanically coupled to second laces 40. Second bladder 38 is mechanically coupled to second stopper 12 at an inlet with second pump 18.

A user can mechanically couple first laces 40 to second laces 40 by tying to creates a series of cavities or holes depending on how closely together right bladder 38 is to left bladder 38. Embodiments of the present invention use "cavity" to refer to either construction even though it is possible for penis 38 to go entirely through the sexual novelty, which may cause the cavity to become then a hole. Once tied, cavities exist between the laces 40 forming small cavity 46, medium cavity 44, and large cavity 42.

Embodiments of the present invention teaches that minor increases in pressure within the bladders 38 can be accomplished by pumping a small amount of air into either bladder 38 with its respective pump 18. This can simulate the movement of muscles in a body orifice that can better simulate sexual intercourse than the prior art.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A sexual novelty configured to pleasure a user by simulating sexual intercourse, the sexual novelty comprising a bladder which can be partially filled with air to create pressure within the bladder; said bladder including a first bladder mechanically coupled to first laces and a second bladder mechanically coupled to second laces, the first and second laces tied together to form a plurality of cavities including a small cavity, a medium cavity and a large cavity, each of said plurality of cavities can accommodate a penis; a pump mechanically coupled to said bladder which can provide slight increase in the pressure within the bladder in order to create different levels of pressure; wherein the penis can move in and out of each of said plurality of cavities to simulate sexual intercourse while the pump can be used to change the pressure during the simulated intercourse.

2. The sexual novelty of claim 1, wherein the plurality of cavities have different sizes to accommodate different cavity preferences.

3. The sexual novelty of claim 1, further comprising:
an inlet detachably mechanically coupled to the bladder and detachably coupled to a stopper wherein the stopper can be removed permitting partial inflation of the bladder with a water source.

4. The sexual novelty of claim 1, further comprising:
an inlet mechanically coupled to the bladder and detachably coupled to a stopper wherein the stopper can be removed permitting partial inflation of the bladder with a water source; and
an outlet mechanically coupled to the bladder and detachably coupled to a second stopper wherein the second stopper can be removed permitting partial deflation of the bladder.

* * * * *